(12) United States Patent
Jeon et al.

(10) Patent No.: US 8,829,205 B2
(45) Date of Patent: Sep. 9, 2014

(54) METHOD FOR PREPARING COUMESTROL AND COUMESTROL PREPARED BY SAME

(75) Inventors: Hee Young Jeon, Yongin-si (KR); Dae Bang Seo, Yongin-si (KR); Si Young Cho, Seoul (KR); Sang Jun Lee, Seongnam-si (KR)

(73) Assignee: Amorepacific Corporation, Seoul (KR)

( * ) Notice: Subject to any disclaimer, the term of this patent is extended or adjusted under 35 U.S.C. 154(b) by 226 days.

(21) Appl. No.: 13/575,267

(22) PCT Filed: Jan. 31, 2011

(86) PCT No.: PCT/KR2011/000673
§ 371 (c)(1),
(2), (4) Date: Jul. 25, 2012

(87) PCT Pub. No.: WO2011/093686
PCT Pub. Date: Aug. 4, 2011

(65) Prior Publication Data
US 2012/0289714 A1 Nov. 15, 2012

(51) Int. Cl.
*C07D 493/00* (2006.01)
*C12P 17/18* (2006.01)

(52) U.S. Cl.
CPC .................................. *C12P 17/181* (2013.01)
USPC .......................................... 549/279; 435/119

(58) Field of Classification Search
USPC .......................................... 549/279; 435/119
See application file for complete search history.

(56) References Cited

U.S. PATENT DOCUMENTS 3,564,019 A * 2/1971 Holmlund et al. ............ 549/279
6,129,937 A  10/2000 Zurbriggen et al.

FOREIGN PATENT DOCUMENTS

| EP | 1 357 807 B1 | 3/2007 |
| JP | 2008-120729 A | 5/2008 |
| KR | 10-0360306 B1 | 11/2002 |
| KR | 10-0706279 B1 | 4/2007 |
| KR | 10-0778938 B1 | 11/2007 |
| WO | WO 01/97769 A1 | 12/2001 |

OTHER PUBLICATIONS

S. M. Boué et al., "Induction of the Soybean Phytoalexins Coumestrol and Glyceollin by Aspergillus," J. Agric. Food Chem., vol. 48, No. 6, pp. 2167-2172, 2000.
X. Hao et a., "Analysis of Coumestrol Content in Soybean." Journal of Beijing University of Agriculture, vol. 23, No. 3, pp. 7-9, 2008.

* cited by examiner

*Primary Examiner* — Nizal Chandrakumar
(74) *Attorney, Agent, or Firm* — Dickstein Shapiro LLP

(57) ABSTRACT

The present invention relates to a method for preparing coumestrol, comprising a step in which beans are germinated and a step in which the beans are fermented, and to coumestrol prepared by the method.

6 Claims, 9 Drawing Sheets

METHOD FOR PREPARING COUMESTROL AND COUMESTROL PREPARED BY SAME

TECHNICAL FIELD

The present disclosure relates to a method for producing coumestrol and coumestrol produced thereby.

BACKGROUND ART

Bean is of great nutritional value and contains various physiologically active and functional substances. Especially, since the phytoestrogens contained in bean are similar to the estrogen of mammals including human in structure, they have the effect of preventing chronic diseases such as hormonal disorders. The phytoestrogens include in general isoflavone, coumestan and lignan.

DISCLOSURE

Technical Problem

The present disclosure is directed to providing a method for producing coumestrol and coumestrol produced thereby.

Technical Solution

In one general aspect, the present disclosure provides a method for producing coumestrol, including: germinating bean; and fermenting the bean.

In another general aspect, the present disclosure provides coumestrol produced by the above method.

Advantageous Effects

The method for producing coumestrol according to the present disclosure enables production of a large amount of coumestrol from bean at high yield by increasing the content of coumestrol in the bean. The method can produce a large amount of coumestrol which is very expensive. The produced coumestrol may be used usefully in the fields of pharmaceuticals, foods or cosmetics.

MODE FOR INVENTION

Figure 1:
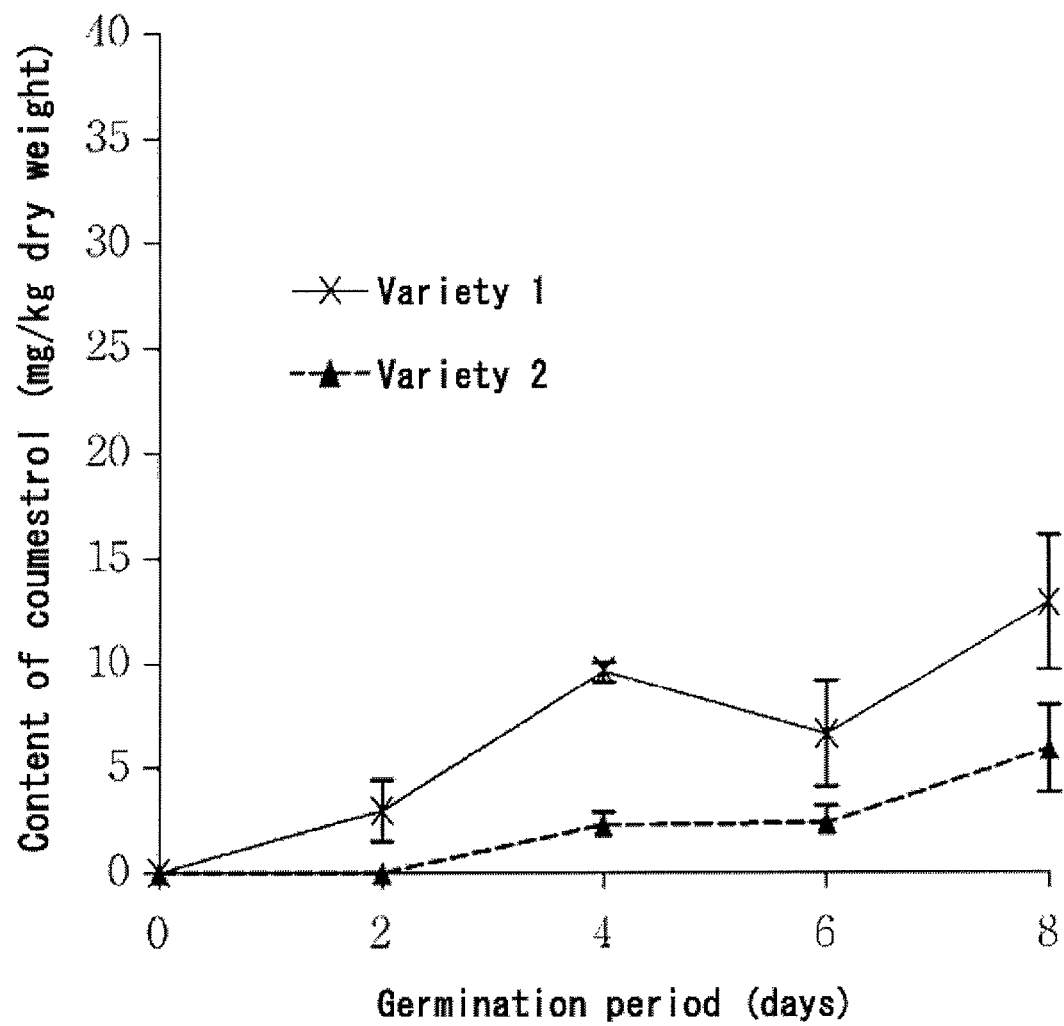
FIG. 1 shows the content of coumestrol (mg/kg dry weight) extracted from bean germinated in an automatic watering apparatus at 30° C.

Coumestrol (CMS; 3,9-dihydroxy-6H-benzofuro(3,2-c)(1)benzopyran-6-one $C_{15}H_8O_5$, MW: 268.2) is a coumarin-like compound structurally similar to the natural estrogen estradiol or stilbestrol. It has a structure of the chemical formula 1:

[chemical formula 1]

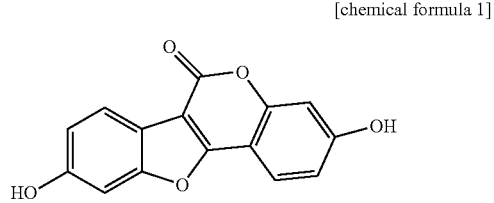 [SMILES: O=c1oc2cc(O)ccc2c2oc3cc(O)ccc3c12]

Since the estrogenic activity of coumestrol is 30-100 times higher as compared to isoflavone which is known to have estrogenic activity, it is very useful in alleviating the symptoms of uterine cancer, bone marrow cancer, breast cancer, brain cancer or menopausal disorders. The estrogenic activity of coumestrol is thought to be attributable to its structure.

Coumestrol is known to be present in very small amounts in bean or other plants in the family Fabaceae. Accordingly, it is necessary to effectively produce the coumestrol which is very useful but is contained in bean in trace amount.

Hereinafter, the present disclosure will be described in more detail.

In an aspect, the present disclosure provides a method for producing coumestrol, comprising: a germinating process of germinating bean; and a fermenting process of fermenting the bean.

In an aspect of the present disclosure, the bean may be any plant in the family Fabaceae that synthesizes coumestrol. For example, the bean that can be used in the present disclosure includes those for paste, bean curd, bean sprouts, bean-mixed rice or unripe bean. The bean species for paste(Jang) or bean curd include daepung, hojang, jangwon, daehwang, sodam, songhak, daewon, jinpum, danbaek, duyu, sinpaldal, taegwang, manri, jangsu, muhan, baekun, saeal, hwanggeum and jangyeop. The species for bean sprouts include sinhwa, sowon, anpyeong, seonam, dachae, sorok, soho, somyeong, dawon, pungsan-namul, iksan-namul, sobaek-namul, gwangan, danyeop and eunha. The species for bean-mixed rice include cheongja, heukcheong, galmi, seonheuk, geomjeong-kong and ilpumgeomjeong-kong. Also, the species for unripe bean include daol, sinrok, saeeul, geomjeongeul, seokryang-putkong, hwaeom-putkong and keuneul.

In another aspect of the present disclosure, the bean may be one that can germinate and is resistant to damage from disease and harmful insects. Examples may include sinhwa-kong, sowon-kong, anpyeong, seonam, dachae, sorok, soho, somyeong, dawon, pungsan-kongnamul, iksan-kongnamul, sobaek-kongnamul, gwangan, danyeop and eunha.

The method for producing coumestrol according to the present disclosure comprises a germinating process of germinating bean. The germinating process may be conducted by contacting the bean at least partly with oxygen or air.

The method for producing coumestrol according to the present disclosure also comprises a fermenting process of fermenting the bean. Coumestrol is known as a phytoalexin synthesized by the plants in the family Fabaceae to protect themselves from attack of fungi or other pathogenic microorganisms. Thus, when bean is contacted with microorganisms such as fungi, yeasts or lactic acid bacteria, they may increase the content of coumestrol in the bean by acting as coumestrol biosynthesis elicitors. In an aspect of the present disclosure, the content of coumestrol in the bean may be increased via the fermenting process of contacting a the bean at least partly with microorganisms. In another aspect of the present disclosure, the fermenting process may be conducted by inoculating the bean with microorganisms 1-10 times, specifically 1-5 times, more specifically 1-3 times. Through this process, the microorganisms may be better contacted with the bean.

In a method for producing coumestrol according to an aspect of the present disclosure, the germinating process and the fermenting process may be conducted simultaneously or successively. In another aspect of the present disclosure, when the germinating process and the fermenting process are conducted simultaneously, the bean may be contacted with oxygen or air in the state where the bean is contacted with microorganisms. Specifically, the bean may be contacted with oxygen or air in the state where the bean is immersed in a medium containing the microorganisms.

In an aspect of the present disclosure, the microorganisms may be any one that can act as coumestrol biosynthesis elicitor. In another aspect of the present disclosure, the microorganism may be fungi, yeasts or lactic acid bacteria. Specifically, the fungus may belong to the genus *Aspergillus*, *Penicillium* or *Monascus*. More specifically, the microorganism may be at least one selected from a group consisting of *Aspergillus niger*, *Aspergillus sojae*, *Aspergillus oryzae* and *Bifidobacterium infantis*. The above-listed microorganisms are adequate for promoting the production of coumestrol by the bean.

In an aspect of the present disclosure, the microorganisms may be contacted with the bean by applying a suspension of the spores of the microorganisms on the surface of the cotyledon of the bean. In another aspect of the present disclosure, the microorganisms may be contacted with the bean by applying a powder of the microorganisms to a medium containing the bean. In another aspect of the present disclosure, 0.05-2 wt %, specifically 0.75-2 wt %, more specifically 1.0-2.0 wt %, of the microorganisms may be contacted based on the total weight of the medium.

In an aspect of the present disclosure, the condition of at least one of the germinating process and the fermenting process is not particularly limited as long as germination and fermentation can be achieved consistently. An exemplary condition of the germinating or fermenting process is as follows.

In an aspect of the present disclosure, at least one of the germinating process and the fermenting process may be conducted in a reactor. In another aspect of the present disclosure, the process may be conducted in a reactor containing 20-80 vol %, specifically 40-60 vol %, more specifically 45-55 vol %, of a medium based on the total volume of the reactor.

In an aspect of the present disclosure, the medium is not particularly as long as the germination and fermentation can be achieved effectively. Specifically, a liquid nutrient medium, more specifically a potato dextrose broth (PDB) medium may be used. In another aspect of the present disclosure, the medium may contain 0.001-10 wt %, specifically 0.1-5 wt %, more specifically 0.5-2 wt % of saccharides based on the total weight of the medium. The saccharides include common monosaccharides, disaccharides or polysaccharides, specifically include sucrose, glucose or SRT.

In an aspect of the present disclosure, the process may be conducted by adding 1-50 vol %, specifically 5-20 vol %, more specifically 6-12 vol % of bean to the reactor based on the total volume of the reactor. During the process, some of the bean may be immersed in the medium and the remainder may not be immersed in the medium. When the bean is completely exposed to air without being immersed in the medium, the microorganisms contacted to ferment the bean may be washed off during watering. Conversely, when the bean is completely immersed in the medium, the germinated bean may rot.

In an aspect of the present disclosure, the process may be conducted while supplying oxygen or air as much as possible. For example, when the process is conducted in a 5000 mL reactor, oxygen or air may be supplied at a rate of 2,500 vvm/m. Also, when the process is conducted in a 3 L reactor, oxygen or air may be supplied at a rate of 15,000 vvm/m. The sufficient supply of oxygen or air may lead to effective germination.

In an aspect of the present disclosure, the process may be conducted at 20 to 35° C., specifically 20 to 30° C. In another aspect of the present disclosure, the process may be conducted in the dark. In another aspect of the present disclosure, the process may be conducted for 2 to 10 days. For example, the germinating process may be conducted for 2 days and then the germinating process and the fermenting process may be conducted simultaneously for 6 to 8 days.

Through the germinating process and the fermenting process conducted under the above-described conditions, the content of coumestrol in the bean may be increased effectively.

A method for producing coumestrol according to an aspect of the present disclosure may further comprise, prior to the germinating process, a sterilizing process of sterilizing the bean with at least one of sterilized water, ethanol and sodium hypochlorite, specifically with sterilized water.

A method for producing coumestrol according to an aspect of the present disclosure may further comprise, after the germinating process and the fermenting process, an extracting process of extracting coumestrol from the germinated and fermented bean. The extraction may be conducted by a method commonly employed in the art, specifically by alcohol extraction, more specifically by ethanol extraction.

In another aspect, the present disclosure provides coumestrol produced by the method for producing coumestrol. The coumestrol may be used usefully in the fields of pharmaceuticals, foods or cosmetics. In another aspect, the present disclosure provides a pharmaceutical, food or cosmetic composition comprising the coumestrol as an active ingredient.

The features and effects of the present disclosure will now be described in detail through examples. The following examples are for illustrative purposes only and not intended to limit the scope of this disclosure.

EXAMPLES 1-6

Germination and Fermentation of Bean

*Glycine max* (L.) Merrill [two varieties; variety 1 (hereinafter, 'variety 1') and variety 2 (hereinafter, 'variety 2')], which is a bean for bean sprouts, was used. After germination, the bean was contacted with microorganisms and it was investigated whether the production of coumestrol is enhanced. The microorganisms used were the fungi *Aspergillus niger* (KCCM 11240, Korean Culture Center of Microorganisms) and *Aspergillus sojae* (KCCM 60354, Korean Culture Center of Microorganisms, non-toxic, food grade) and the lactic acid bacterium *Bifidobacterium infantis* (KCCM 11207, Korean Culture Center of Microorganisms). Specific experimental conditions are as follows.

<Germinating Condition>

The bean was germinated at 30° C. with humidity fixed at 55%, in the dark. Three groups were tested 2 times per each. Watering was performed automatically for 3 minutes using a timer, with 4-hour intervals. An automatic watering apparatus designed such that water can be drained through a meshed bottom was used.

<Preparation of Microorganisms>

1. Preparation of Fungi (*Aspergillus niger* and *Aspergillus sojae*)

After inoculating a plate medium (potato dextrose agar, Difco™, BD Diagnostics, Sparks, Md., USA) with the microorganisms, the microorganisms were cultured for 2 weeks at 37° C. such that spores were formed sufficiently. The spores were uniformly dispersed in water using a sterilized spatula. Then, after measuring concentration using a hemocytometer, a spore suspension was prepared by diluting the spores to $10^6$ spores/mL.

2. Preparation of Lactic Acid Bacterium (*Bifidobacterium infantis*)

After inoculating a sterilized liquid medium (reinforced clostridial medium, Oxoid Ltd, Hampshire, England) with the microorganisms, followed by nitrogen injection and sealing, the microorganisms were cultured for 1 week at 37° C.

<Germination and Treatment with Microorganisms>

The conditions of germination and microorganism treatment for the respective examples are as follows.

TABLE 1

| No. | Treatment condition |
| --- | --- |
| Example 1 | The bean was germinated for 8 days in an automatic watering apparatus without inoculation of microorganisms (see FIG. 1). |
| Example 2 | 100 μL of the spore suspension was inoculated at the seedling of the bean that germinated for 2 days in an automatic watering apparatus, followed by one more inoculation 4 hours later. After the inoculation of *Aspergillus niger*, the bean was further germinated for 2, 4 and 6 days in an automatic watering apparatus (see FIG. 2). |
| Example 3 | 100 μL of the spore suspension ($10^6$ spores/mL, *Aspergillus niger*) and 4 surface-sterilized germinated beans were added together in a glass bottle (Ø 30 mm × h 75 mm) containing 1 mL of a liquid medium (potato dextrose broth, Difco ™, BD Diagnostics, Sparks, MD, USA). Then, the bean was further germinated for 2, 4 and 6 days at 30° C. (see FIG. 3). |
| Example 4 | Experiment was performed in the same manner as in Example 3 except for culturing the germinated bean together with *Aspergillus sojae* (see FIG. 4). |
| Example 5 | Experiment was performed in the same manner as in Example 3 except for culturing the germinated bean together with *Bifidobacterium infantis* (see FIG. 5). |
| Example 6 | 4 surface-sterilized germinated beans were completely immersed in a glass bottle (Ø 30 mm × h 75 mm) containing 5 mL of a liquid medium (potato dextrose broth, Difco ™, BD Diagnostics, Sparks, MD, USA). Then, after adding 100 μL of the spore suspension ($10^6$ spores/mL), the bean was further germinated for 2, 4 and 6 days at 30° C. |

<Analysis of Coumestrol Content>

Ethanol was added to the germinated bean to a final concentration of 80%. After homogenization, coumestrol was extracted and analyzed.

Column: NOVA-PAK RP18 5 μm (3.9×150 mm)
Column temperature: 27° C.
Detector: UVD (260 nm)
Solvent: 1% acetic acid in water (acetonitrile gradient)

<Experimental Result>

EXAMPLE 1

In Example 1, the bean was germinated without inoculation of microorganisms. As seen from FIG. 1, the content of coumestrol was very low.

EXAMPLE 2

Figure 2:
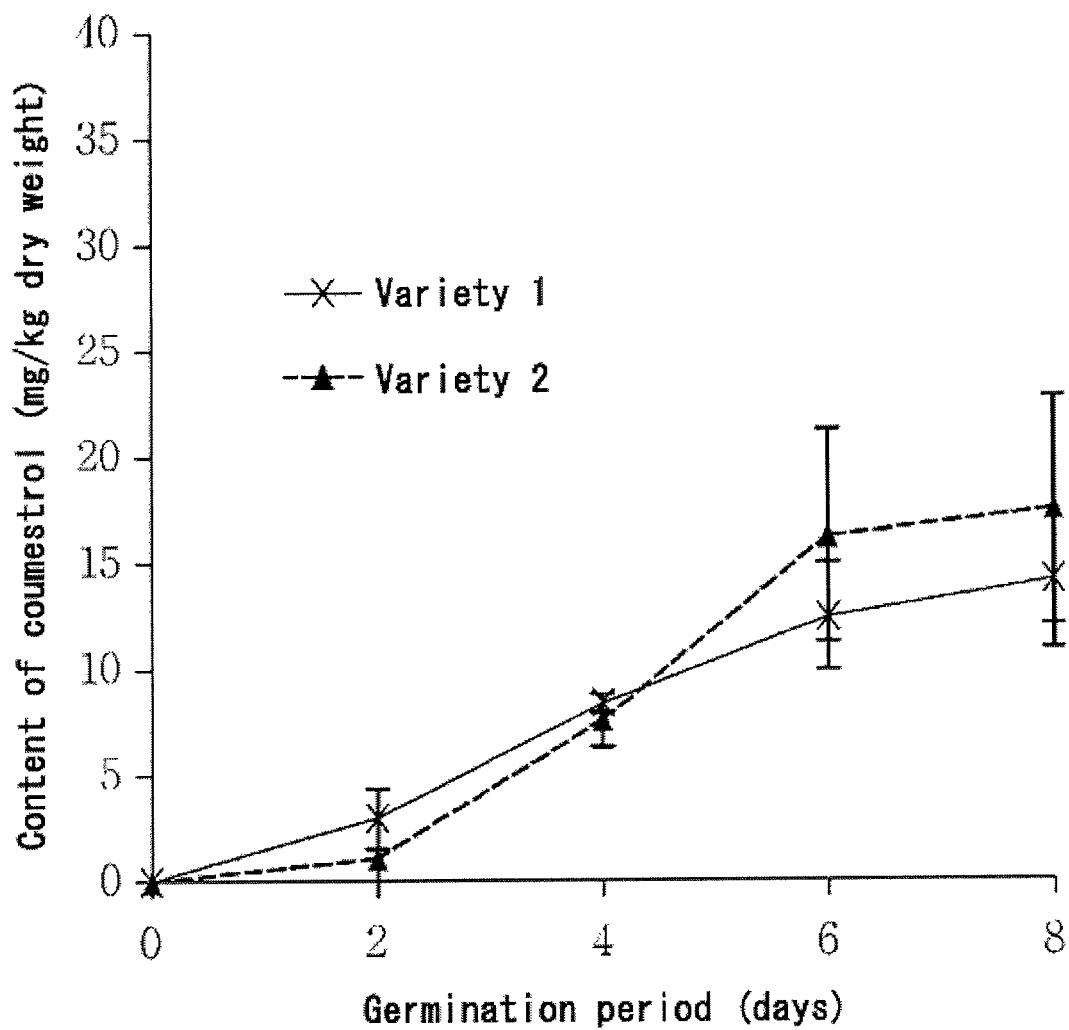
FIG. 2 shows the content of coumestrol (mg/kg dry weight) extracted from bean germinated after contacting with *Aspergillus niger;*

When the bean was germinated and inoculated with the microorganisms, the production of coumestrol was higher than Example 1, as seen from FIG. 2.

But, since the microorganisms were inoculated on the surface of the seedling, the inoculated microorganisms did not effectively act as coumestrol biosynthesis elicitors. It may be because the inoculated microorganisms could not grow fully but were washed off due to the watering conducted with 4-hour intervals. Indeed, the growth of microorganisms was not observed in the bean grown for 8 days.

Through this example, it was confirmed that the microorganisms can act as an efficient coumestrol biosynthesis elicitor for bean. Also, it was confirmed that adequate supply of water is important for the growth of bean.

EXAMPLE 3

Figure 3:
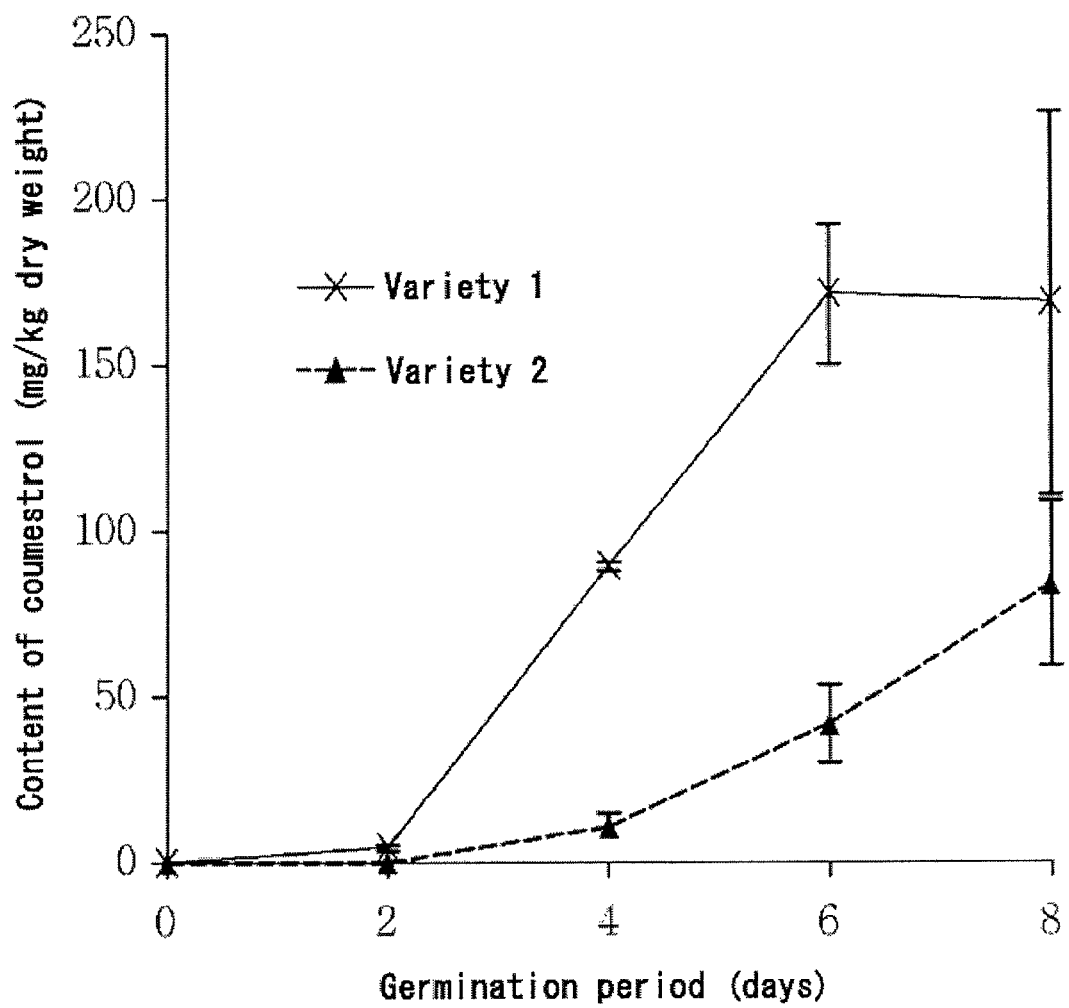
FIG. 3 shows the content of coumestrol (mg/kg dry weight) extracted from bean germinated in liquid medium (potato dextrose broth) at 30° C. after contacting with *Aspergillus niger;*

When the bean germinated for 2 days was cultured together with *Aspergillus niger*, the production of coumestrol was remarkably increased up to about 170 mg/kg dry weight for the variety 1 on day 6 and up to 82.4 mg/kg dry weight the variety 2 on day 8, as seen from FIG. 3. This corresponds to about 13-fold increase as compared to Example 1 wherein the bean was grown in the automatic watering apparatus without inoculation of microorganisms [12.80 mg/kg dry weight (variety 1) and 5.85 mg/kg dry weight (variety 2)]. Through this example, it was confirmed that the production of coumestrol by bean can be increased by inoculation of *Aspergillus niger*.

EXAMPLE 4

Figure 4:
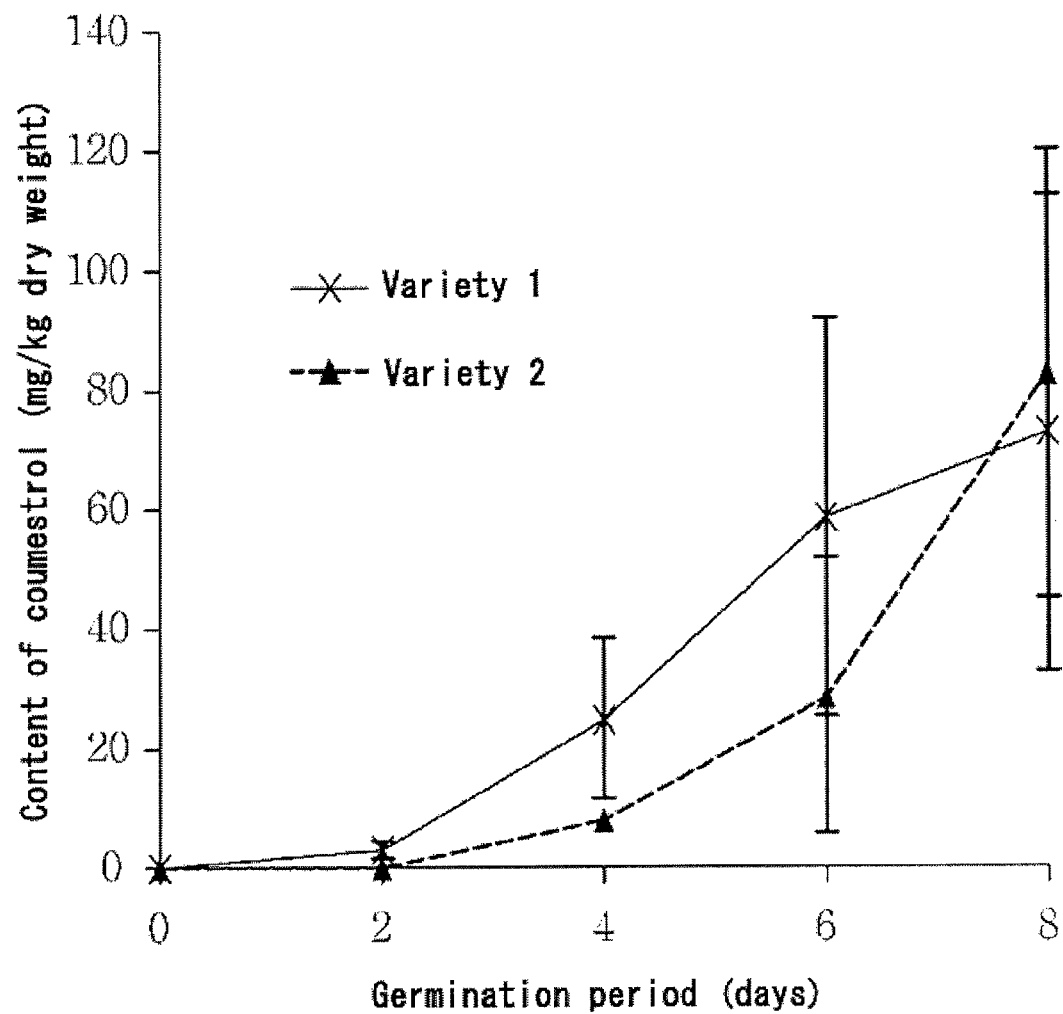
FIG. 4 shows the content of coumestrol (mg/kg dry weight) extracted from bean germinated in liquid medium (potato dextrose broth) at 30° C. after inoculating with *Aspergillus sojae;*

When the bean germinated for 2 days was cultured together with *Aspergillus sojae*, the production of coumestrol was 72.04 mg/kg dry weight for the variety 1 and 81.63 mg/kg dry weight for the variety 2, as seen from FIG. 4. The production of coumestrol was significantly higher as compared to Example 1 but was relatively lower than when the bean was cultured together with *Aspergillus niger*. Through this example, it was confirmed that the production of coumestrol by bean is dependent on the kind of microorganisms used.

EXAMPLE 5

Figure 5:
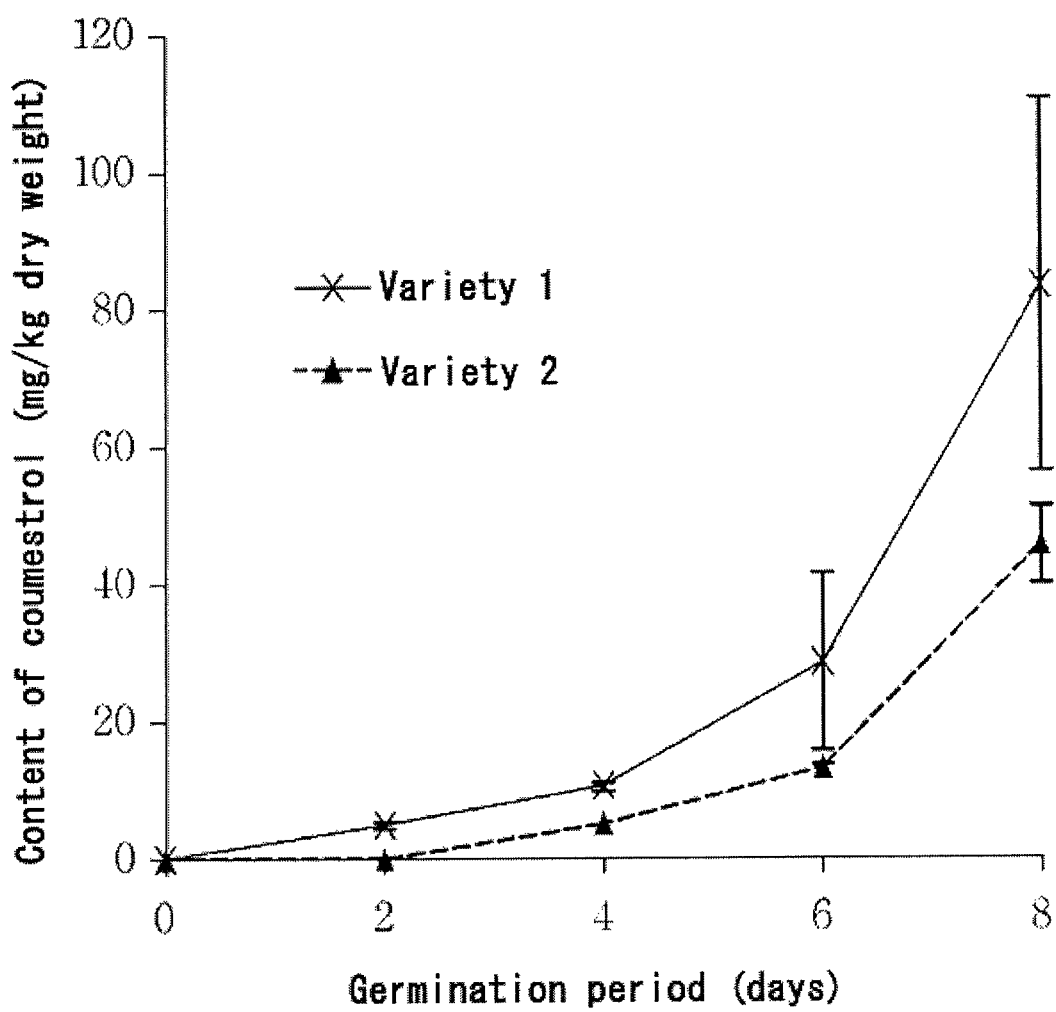
FIG. 5 shows the content of coumestrol (mg/kg dry weight) extracted from bean germinated in liquid medium (potato dextrose broth) at 30° C. after inoculating with *Bifidobacterium infantis;*

When the bean was cultured together with the lactic acid bacterium *Bifidobacterium infantis* for 4 days, the production of coumestrol was increased to 82.85 mg/kg dry weight for the variety 1 and 45.1 mg/kg dry weight for the variety 2, as seen from FIG. 5.

EXAMPLE 6

Under this experimental condition, the bean was not germinated well since it was completely immersed in the medium. Upon treatment with microorganisms, the bean rotted and coumestrol was not detected at all.

EXAMPLE 7

Large-scale Production

1. Method

Coumestrol was produced using a large-volume bioreactor under various conditions. All appliances were sterilized using a high-pressure sterilizer at 121° C. before inoculation of microorganisms. Pungsan-namul kong or sowon kong was used as the bean. The seeds of bean were sterilized by washing 2 times with at least one selected from sterilized water, ethanol and sodium hypochlorite. A medium containing at least one of 1% sucrose, 1% glucose and 1% SRT was prepared with an amount of 20 to 80 vol % based on the reactor volume. 3-12 vol % of the seeds of bean were added based on the reactor volume. The bean was germinated in the reactor containing the medium and the bean seeds at 20-30° C., in the light or in the dark, under supply of air at 15000 vvm/m.

When the bean began to germinate on day 2, 0 to 1.25 wt % of microorganisms ($1 \times 10^9$ CFU/g *Aspergillus oryzae*; available from Mediogen) based on the total weight of the medium were added to the medium and cultured until day 8.

After the culturing, coumestrol was extracted from the bean and the medium and analyzed in the same manner as in Examples 1 to 6.

2. Result (1) Result According to Varieties of Bean

Figure 6:
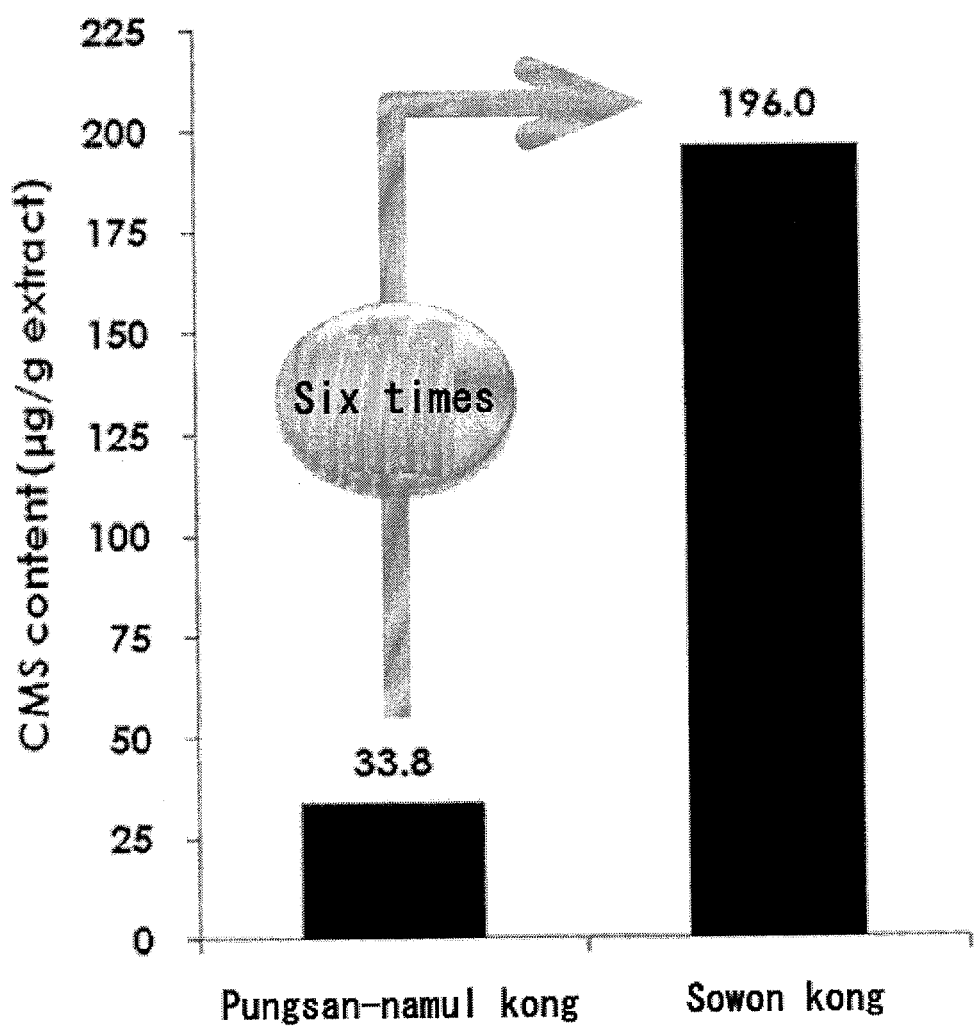
FIG. 6 shows the content of coumestrol in different varieties of bean.

The content of coumestrol according to the varieties of bean is shown in FIG. 6. As seen from FIG. 6, about 33.8 μg/g of coumestrol was produced from pungsan-namul kong and about 196 μg/g of coumestrol was produced from sowon kong. Considering that 5 μg/g or less of coumestrol is naturally produced from the bean, it can be seen that the present disclosure enables the production of coumestrol in large quantities.

(2) Result According to Medium Additives

Figure 7:
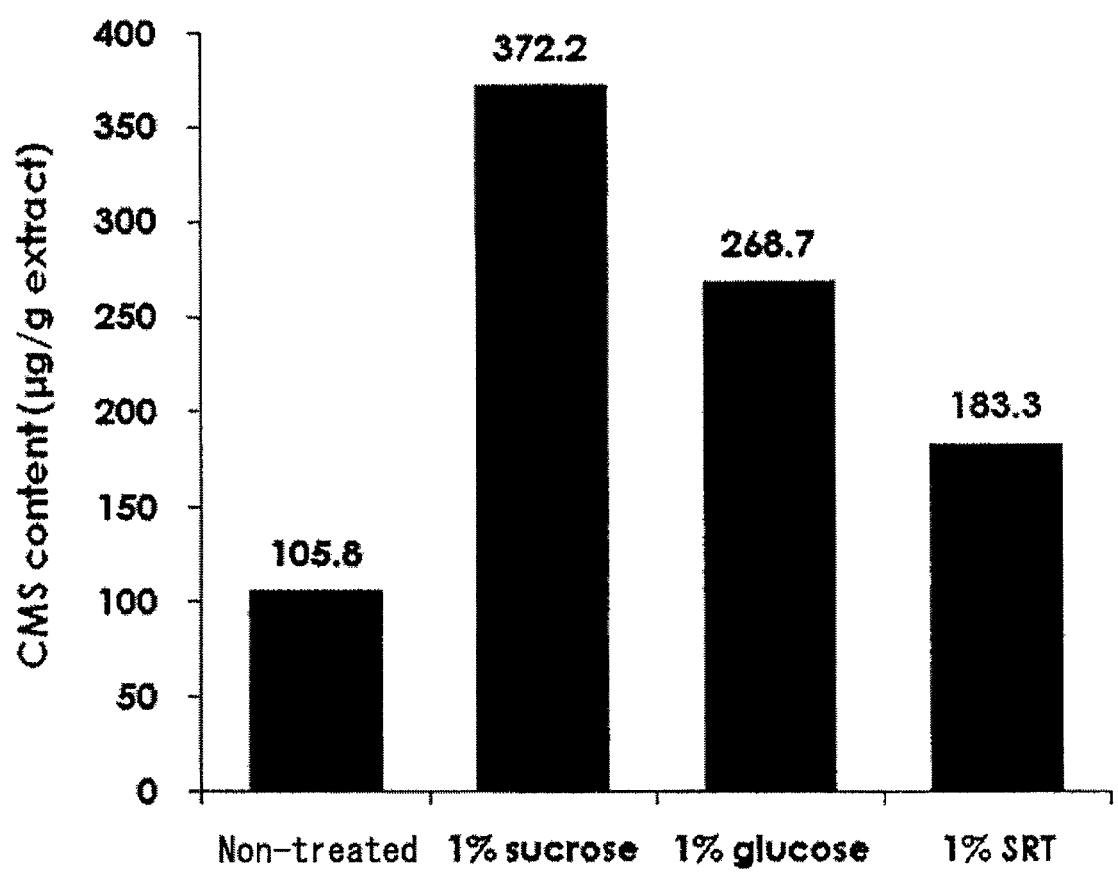
FIG. 7 shows the content of coumestrol depending on medium additives.

The content of coumestrol according to addition of the medium containing at least one of 1% sucrose, 1% glucose and 1% SRT is shown in FIG. 7. As seen from FIG. 7, more coumestrol was produced when the additive was added as compared to the non-treated group. In particular, the production of coumestrol was highest when the medium contained 1% sucrose. It is thought that the additives support the growth of the microorganisms so that they can act as coumestrol biosynthesis elicitor.

(3) Result According to Concentration of Microorganisms

Figure 8:
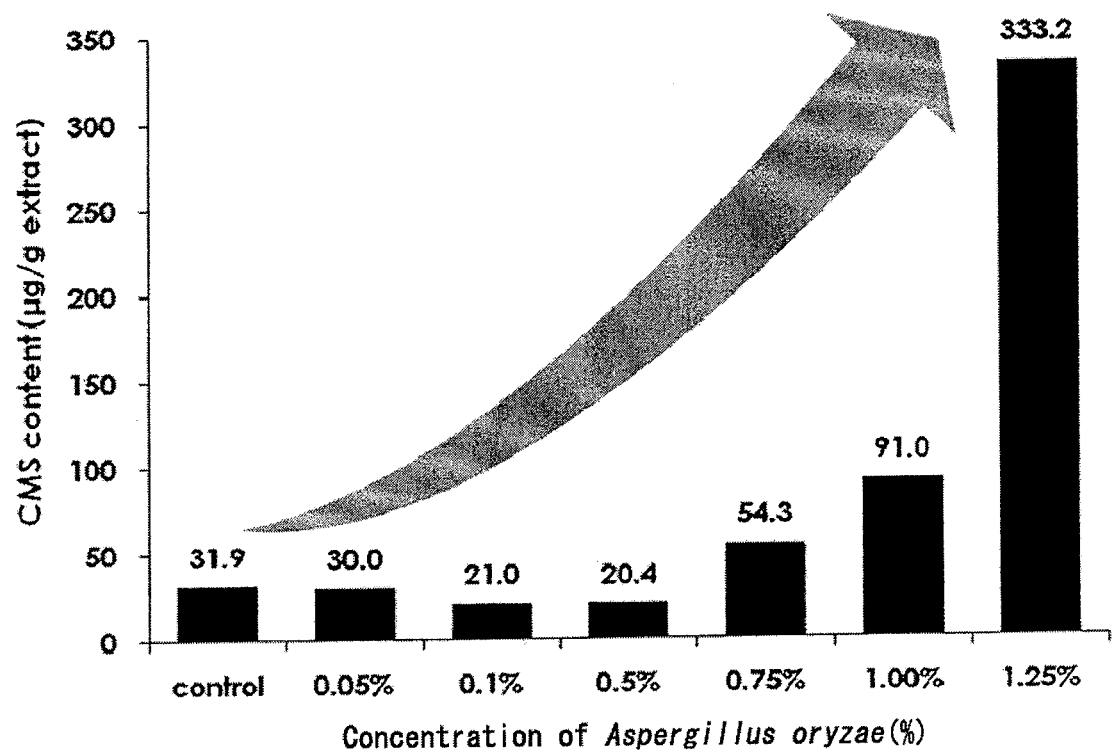
FIG. 8 shows the content of coumestrol depending on the concentration of fungus.

The content of coumestrol according to the concentration of the microorganisms that act as coumestrol biosynthesis elicitor is shown in FIG. 8. As seen from FIG. 8, when the concentration of the microorganisms was above some level, more coumestrol could be produced as the concentration increased. In particular, the production of coumestrol was about 11 times higher than the non-treated group when the concentration of the microorganisms was 1.25 wt %. Meanwhile, when the concentration of the microorganisms was 2 wt % or higher, germination did not occur but only fermentation occurred.

(4) Optimized Condition

The production of coumestrol was compared while combining the above-described conditions. The optimized condition is as follows.

TABLE 2

| | Optimized condition |
|---|---|
| Variety of bean | Sowon kong |
| Sterilizer | Sterilized water |
| Quantity of bean | 10 vol % based on reactor volume |
| Quantity of medium | 50 vol % based on reactor volume |
| Medium additive | 1% sucrose |
| Temperature | 25° C. |
| Brightness | Dark |
| Supply of air | Maximum (15,000 vvm/m for 3 L reactor) |

Figure 9:
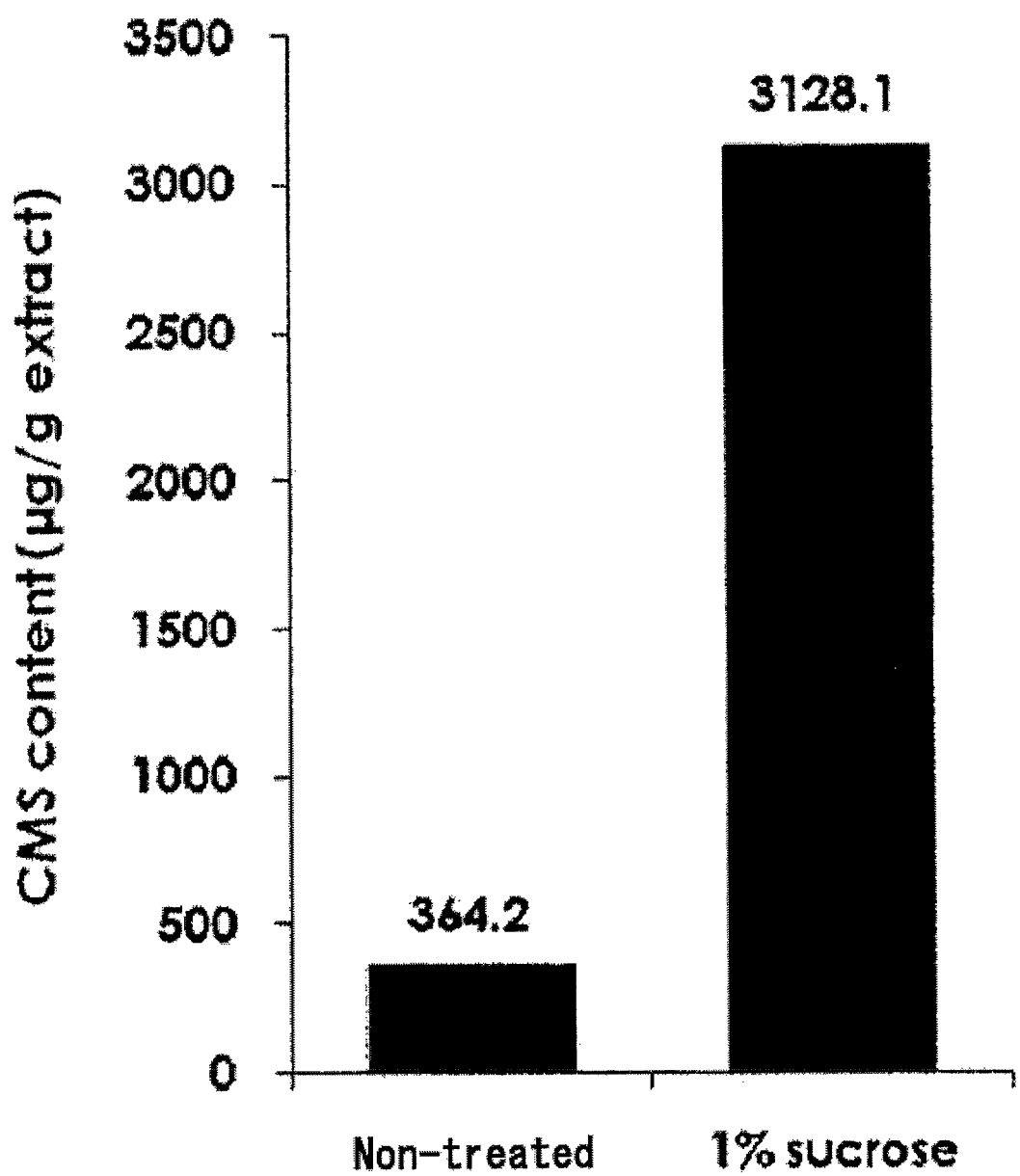
FIG. 9 shows the content of coumestrol under the optimized condition.

The content of coumestrol produced under the optimized condition is shown in FIG. 9. As seen from FIG. 9, 8 times more coumestrol could be produced under the optimized condition.

Through the above examples, it was confirmed that the content of coumestrol in bean can be increased by germinating the bean and fermenting it using microorganisms. Further, it was confirmed that coumestrol can be produced in commercial scale under optimized germinating and fermenting conditions.

The invention claimed is:

1. A method for producing coumestrol, comprising:
   contacting a bean at least partly with oxygen or air to germinate the bean; and
   contacting the bean at least partly with microorganisms to ferment the bean,
   wherein the microorganisms are fungi, yeasts or lactic acid bacteria, and wherein the bean is contacted with oxygen or air in the state where the bean is contacted with microorganisms by being immersed in a medium containing the microorganisms to simultaneously germinate and ferment the bean.

2. The method for producing coumestrol according to claim 1, wherein the fungus belongs to the genus *Aspergillus, Penicillium* or *Monascus*.

3. The method for producing coumestrol according to claim 1, wherein the microorganism is at least one selected from a group consisting of *Aspergillus niger, Aspergillus sojae, Aspergillus oryzae* and *Bifidobacterium infantis*.

4. The method for producing coumestrol according to claim 1, wherein at least one of said contacting bean at least partly with oxygen or air and said contacting the bean at least partly with microorganisms is conducted in a reactor containing 20-80 vol % of a medium based on the total volume of the reactor with 1-50 vol % of the bean based on the total volume of the reactor.

5. The method for producing coumestrol according to claim 4, wherein the medium contains 0.001-10 wt % of saccharides based on the total weight of the medium.

6. The method for producing coumestrol according to claim 1, wherein at least one of said contacting bean at least partly with oxygen or air and said contacting the bean at least partly with microorganisms is conducted at 20-35 ° C. in the dark for 2-10 days.

* * * * *